United States Patent
Yanaka et al.

(10) Patent No.: US 6,211,175 B1
(45) Date of Patent: Apr. 3, 2001

(54) CARDIAC DISEASES IMPROVING METHOD

(75) Inventors: Mikiro Yanaka, Matsudo; Fuyuhiko Nishijima; Mikio Sugano, both of Tokyo; Hiroshi Takahashi, Houya; Shigeru Suzuki, Yamato; Hiroyuki Enari, Tokyo; Michihito Ise, Kawashima-machi, all of (JP)

(73) Assignee: Kureha Chemical Industry Co., Ltd. (JP)

( * ) Notice: Subject to any disclaimer, the term of this patent is extended or adjusted under 35 U.S.C. 154(b) by 0 days.

(21) Appl. No.: 09/166,759

(22) Filed: Oct. 6, 1998

Related U.S. Application Data

(63) Continuation of application No. 08/991,411, filed on Dec. 16, 1997.

(30) Foreign Application Priority Data

Jan. 21, 1997 (JP) ........................................ 9-20925

(51) Int. Cl.$^7$ ...................... A61K 31/495; A61K 31/535
(52) U.S. Cl. .................... 514/237.5; 514/231.8; 514/236.2; 514/235.5; 514/255
(58) Field of Search ............................... 514/237.5, 235.5

(56) References Cited

U.S. PATENT DOCUMENTS

| 5,128,355 | 7/1992 | Carini et al. . |
| 5,153,197 | 10/1992 | Carini et al. . |
| 5,155,118 | 10/1992 | Carini et al. . |
| 5,696,118 | 12/1997 | Yanaka et al. . |
| 5,731,310 | 3/1998 | Yanaka et al. . |
| 5,739,131 | 4/1998 | Yanaka et al. . |

FOREIGN PATENT DOCUMENTS

| 205 901 | 1/1984 | (DD) . |
| 27 33 156 A1 | 2/1978 | (DE) . |
| 0 138 720 A2 | 4/1985 | (EP) . |
| 0 253 310 A2 | 1/1988 | (EP) . |
| 0 253 310 A3 | 8/1990 | (EP) . |
| 0 475 206 A2 | 3/1992 | (EP) . |
| 0 475 206 A3 | 8/1992 | (EP) . |
| 0 588 299 A2 | 3/1994 | (EP) . |
| 0 588 299 A3 | 6/1994 | (EP) . |
| 0 685 470 A2 | 6/1995 | (EP) . |
| 0 685 470 A3 | 7/1996 | (EP) . |
| 0 807 628 A1 | 11/1997 | (EP) . |

OTHER PUBLICATIONS

D.M. Pollock et al., "Angiotensin II Receptor Blockade Improves Renal Function in Rats with Reduced Renal Mass" *J. Pharm. and Experimental Therapeutics* 267(2):657–663 (1993).

*Primary Examiner*—Robert W. Ramsuer
(74) *Attorney, Agent, or Firm*—Testa, Hurwitz & Thibeault, LLP

(57) ABSTRACT

This invention relates to cardiac diseases improving agents substantially free from antagonistic action to type 1 receptor of angiotensin II which participates to hypotensive action. Particularly, this invention relates to cardiac diseases improving agents composed of effective ingredients of aromatic compounds or pharmacologically acceptable salts thereof shown by below mentioned general formula.
Chemical formula 1

[General formula (I)]

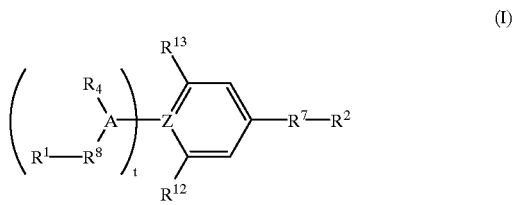

(wherein, substituents thereof typically include, $R^1$, $R^4$, $R^{13}$ representing hydrogen atom, an alkyl group, a haloalkyl group and so forth, $R^8$ representing —CO—, —$SO_2$— or single bond, $R^2$ representing a 3–7 membered aliphatic cyclic amino group having at least one nitrogen atom, $R^7$ representing —CO—or —$SO_2$—, and $R^{12}$ representing N-substituted valeramido group.)

7 Claims, No Drawings

CARDIAC DISEASES IMPROVING METHOD

The following is a continuation of co-pending U.S. Ser. No. 08/991,411, filed Dec. 16, 1997.

FIELD OF THE INVENTION

This invention relates to cardiac diseases improving agents containing effective ingredients of aromatic compounds or pharmacologically acceptable salts thereof.

The cardiac diseases improving agents of the present invention exert sufficient improving effects against cardiac diseases despite of substantially null or very weak antagonistic action to type 1 angiotensin II receptor which participates to hypotensive action.

BACKGROUND OF THE INVENTION

Patients with cardiac diseases recently show a rapid increasing tendency. One major cause is a delay of development of definitive drug for the treatment of cardiac diseases in addition to the increasing population of aged persons and changes of living environments. Cardiac diseases such as cardiac failure, cardiac hypertrophy, abnormal heart rate and valvular diseases have been mainly managed with symptomatic treatment of lesions including prevention of cardiac hypertrophy with a hypotensive agent, diet or exercise therapy. Particularly, cardiac diseases often accompanies with hypertension which is suspected to be one of a cause of aggravation, thus, hypotensive agents have been generally used. Among them, inhibitors of production or action of angiotensin II have often been tried because angiotensin II elevates blood pressure and stimulates proliferation of interstitial cells of heart causing aggravation of cardiac diseases. Therefore, elimination of these factors as far as possible is expected to improve the symptoms of cardiac diseases and determinative therapeutic drugs for cardiac diseases have been eagerly awaited.

An agent for inhibiting the enzyme which converts angiotensin I to a pressor angiotensin II, that is angiotensin converting enzyme (ACE) inhibitor (ACEI) such as Enalapril or Captopril® has been used as a hypotensive. These hypotensives are reported to lower blood pressure and improve the progress of renal dysfunction (J. Clin. Pharmacol., 30:155–158, 1990). However, these drugs are pointed out to cause dry cough or adverse reaction of acute renal failure accompanied with hypotensive action and require careful administration [The Saishin-Igaku (Modern Therapy), 48: 1404–1409, 1993].

In addition, an angiotensin II receptor antagonist (AGIIRA) was developed as a hypotensive. Two type 1 and 2 receptors of angiotensin II have been known. The type 1 has been known to participate in blood pressure, however, the action of type 2 has not thoroughly been elucidated, thus, an antagonist of type 1 receptor became a target for the development of hypotensive agent. A hypotensive imidazole derivative having potent antagonistic action to angiotensin II receptor, 2-butyl-4-chloro-5-(hydroxymethyl)-1-[[2'-(1H-tetrazol-5-yl)biphenyl-4-yl]methyl]imidazole (DuP 753 or MK 954) has been known. Its action on renal diseases has already been investigated.

Furthermore, compounds having similar chemical structure with that of above mentioned imidazole derivative have been disclosed in specifications, for example, Published Japanese Unexamined Patent Application No. 23,868 (1988), and U.S. Pat. Nos. 5,128,355, 5,153,197 and 5,155,118. These compounds are disclosed to be effective to hypertension and congestive heart failure in Published Japanese Unexamined Patent Application No. 23,868 (1988), effective to hypertension in U.S. Pat. No. 5,153,197, effective to cardiac failure in U.S. Pat. No. 5,128,355, and effective in renal failure caused by non-steroidal antiinflammatory drugs (NSAIDs) in U.S. Pat. No. 5,155,118, respectively. However, all these imidazole derivatives have characteristic potent angiotensin II receptor antagonistic action and exhibit hypotensive action.

In addition, compounds having benzene structure are disclosed in, for example, EP058829A2 and EP0475206A2 and their indication to renal diseases are also disclosed. However, these benzene compounds have characteristic features of potent angiotensin II receptor antagonistic action accompanying hypotensive action. Administration of a benzene analogue, 2-[N-propyl-N-[[2'-(1H-tetrazol-5-yl)biphenyl-4-yl]methyl]amino]-pyridine-3-carboxylic acid (A-81988), to rats with renal diseases was reported to show improvement in proteinuria accompanied with hypotension (J. Pharmacol. Exp. Ther., 267: 657–663, 1993). That is, the above mentioned benzene analogues exhibit hypotensive action because of potent type 1 receptor antagonistic action and are likely to lead to acute renal failure by application to patients with renal diseases.

Cardiac failure is a final stage in cardiac diseases with progressive symptoms and very poor prognosis of 50% survival rate within five years. Their treatment is classified in acute and chronic phases.

Treatment in acute phase is mainly composed of countermeasures to sudden failure of cardiac pump function and administration of cardiotonics.

On the other hand, chronic phase treatment is focused to arrest the progress of diseases and improve the quality of life (QOL). Under these situation, administration of cardiotonics in a similar manner to that of acute phase often leads to insufficient therapeutic effect or aggravation of the prognosis. At present, it is clear that angiotensin converting enzyme inhibitors (ACEIs) solely improve the prognosis.

However, some administration of angiotensin converting enzyme inhibitors (ACEIs) caused hypotension as mentioned above and led to adverse reactions such as dry cough and acute renal failure.

Treatment of cardiac diseases with conventional hypotensives basically requires potent hypotensives as far as possible. Though hypertension is an important symptom to be treated in cardiac diseases, not only to lower blood pressure but also to maintain appropriate blood pressure is important. Control of blood pressure by various combination of hypotensives at suitable dosages according to the symptoms are necessary. While cardiac diseases per se is desirably treated continuously with sufficient dosage, blood pressure control and effective treatment of cardiac diseases are essentially incompatible in the treatment with a sole drug. The inventors of the present invention have been investigating to find novel unknown characteristic compounds which exhibit sufficient improvement in renal disturbances and devoid of action on blood pressure, and found novel benzene derivatives with antagonistic action to type 1 receptor of angiotensin II at ratios of 1/100 to 1/1,000 or less to those of typical hypotensives and with sufficient improvement in renal disturbances without substantial antagonistic action [Published Japanese Unexamined Patent Application No. 48,651 (1996) and Japanese Patent Application No. 148,382 (1996)].

The inventors of the present invention further investigated the pharmacological action of these benzene derivatives and found that these compounds not only improve renal failure, but also improve symptoms of cardiac diseases such as cardiac failure, while maintaining moderate blood pressure without lowering blood pressure. The present invention is accomplished on the bases of above mentioned characteristic results.

SUMMARY OF THE INVENTION

Thus, one object of the present invention is to provide novel cardiac disease improving agents which maintain moderate blood pressure without lowering blood pressure and improve cardiac diseases.

The present invention relates to cardiac disease improving agents containing effective ingredients of aromatic compounds shown by the following general formula (I) or pharmacologically acceptable salts thereof.
Chemical formula 3
[General formula (I)]

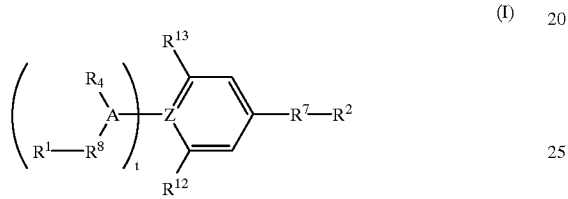

[wherein, $R^1$ represents hydrogen atom, an alkyl group having 1–8 carbon atoms, a haloalkyl group having 1–8 carbon atoms, $-NH_2$ or $-NHR^{21}$; $R^2$ represents hydroxyl group, $-OR^{22}$, a 3–7 membered saturated aliphatic cyclic amino group optionally interrupted with nitrogen atom, oxygen atom or sulfur atom, a 3–7 membered saturated aliphatic cyclic amino group containing at least one nitrogen atom substituted with an alkyl group having 1–8 carbon atoms or a haloalkyl group having 1–8 carbon atoms in the ring, a 3–7 membered saturated aliphatic cyclic alkyl group containing at least one nitrogen atom optionally substituted with an alkyl group having 1–8 carbon atoms or a haloalkyl group having 1–8 carbon atoms in the ring, $-NHR^{23}$, $-N(R^{24})_2$, or $-NH_2$; $R^4$ represents hydrogen atom, an alkyl group having 1–8 carbon atoms, or $-C(=O)R^{25}$; $R^7$ represents $-CO-$ or $-SO_2-$; $R^8$ represents $-CO-$ or single bond; $R^{12}$ represents $-R^{11}-R^5$; $-R^{11}$ represents $-N(R^5)-$, $-NH-$, $-O-$, $-N(R^{26})-$, $-N[C(=O)R^{27}]-$, $-N[C(=O)NH_2]-$ or $-N[C(=O)NHR^{28}]-$; $R^5$ represents hydrogen atom, $-CH_2C_6H_4COOH$, $-CH_2C_6H_4COOR^{31}$, $-CH_2C_6H_4OH$, $-CH_2C_6H_4OR^{32}$, $-CH_2C_6H_4NH_2$, $-CH_2C_6H_4N(R^{33})_2$, $-CH_2C_6H_4$-azole, $-CH_2C_6H_4NHR^{34}$, or $-CH_2C_6H_4C_6H_4R^{14}$; $R^{14}$ represents an azole group or $-COOH$; $R^{13}$ represents hydrogen atom, an alkyl group having 1–6 carbon atoms, a haloalkyl group having 1–6 carbon atoms, $-NHC(=O)(CH_2)_mC_6H_5$, $-NHC(=O)R^{29}$, $-NHC(=O)CH(C_6H_5)_2$, $-NH_2$, $-NHR^{30}$, or $-(CH_2)_nC_6H_5$; Z represents C, CH, or N; A represents CH, or N; $R^{14}$ represents an azole group, or $-COOH$; $R^{21}$, $R^{22}$, $R^{23}$, $R^{24}$, $R^{25}$, $R^{26}$, $R^{27}$, $R^{28}$, $R^{29}$, $R^{30}$, $R^{32}$, $R^{33}$ and $R^{34}$ each independently represents an alkyl group having 1–8 carbon atoms, or a haloaklyl group having 1–8 carbon atoms; $R^{31}$ represents an allyl group having 1–8 carbon atoms, a haloalkyl group having 1–8 carbon atoms, $-(CH_2)_m NR^{35}R^{36}$, $-(CH_2)_nR^{37}$, $-(CH_2)_pCH(NR^{38}R^{39})$ $COOR^{40}$, $-R^{41}-COOR^{42}$, $-CH(R^{43})OC(=O)R^{44}$ or $-CH(R^{45})OC(=O)OR^{46}$; $R^{37}$ represents a 3–7 membered saturated aliphatic cyclic amino group optionally interrupted with nitrogen atom, oxygen atom or sulfur atom, a 3–7 membered saturated aliphatic cyclic amino group containing at least one nitrogen atom substituted with an alkyl group having 1–8 carbon atoms or a haloalkyl group having 1–8 carbon atoms in the ring, a 3–7 membered saturated aliphatic cyclic alkyl group having at least one nitrogen atom optionally substituted with an alkyl group having 1–8 carbon atoms or a haloalkyl group having 1–8 carbon atoms or a 3–7 membered unsaturated heterocyclic group; $R^{44}$ and $R^{46}$ represent $-(CH_2)_rR^{47}$; $R^{47}$ represents hydrogen atom, an alkyl group having 1–8 carbon atoms, a haloalkyl group having 1–8 carbon atoms, $NR^{48}R^{49}$, or a 3–8 membered saturated aliphatic cyclic alkyl group; $R^{41}$ represents a 3–6 membered saturated aliphatic cyclic alkylene group containing at least one nitrogen atom optionally substituted with an alkyl group having 1–6 carbon atoms or a haloalkyl group having 1–6 carbon atoms in the ring; $R^{35}$, $R^{36}$, $R^{38}$, $R^{39}$, $R^{40}$, $R^{42}$, $R^{43}$ and $R^{45}$ each independently represents hydrogen atom, an alkyl group having 1–8 carbon atoms, or a haloalkyl group having 1–8 carbon atoms; m, n, p, q and r each independently represents 0 or an integer of 1–6; t represents 0 or 1, with a proviso when Z represents N, then $R^5$ represents hydrogen atom, $-CH_2C_6H_4COOH$, $-CH_2C_6H_4COOR^{31}$, $-CH_2C_6H_4OH$, $-CH_2C_6H_4OR^{32}$, $-CH_2C_6H_4NH_2$, $-CH_2C_6H_4N(R^{33})_2$, $-CH_2C_6H_4$-azole or $-CH_2C_6H_4NHR^{34}$].

Among them, A, Z and R in the general formula (I) are used to represent the following meanings, and the following compounds (hereinafter may be referred as compounds I) are known compounds and the inventors of the present invention found that they satisfactorily improve renal disorders despite of very low activity to blood pressure [Published Japanese Unexamined Patent Application No. 48,651 (1996)].

These compounds include cardiac diseases improving agents of aromatic compounds or pharmacologically acceptable salts thereof wherein, $R^1$ represents hydrogen atom, an alkyl group having 1–8 carbon atoms, a haloalkyl group having 1–8 carbon atoms, $-NH_2$ or $-NHR^{21}$; $R^2$ represents hydroxyl group, $-OR^{22}$, a 3–7 membered saturated aliphatic cyclic amino group optionally interrupted with nitrogen atom, oxygen atom or sulfur atom, $-NHR^{23}$, $-N(R^{24})_2$, or $-NH_2$; $R^4$ represents hydrogen atom, an alkyl group having 1–8 carbon atoms, or $-C(=O)R^{25}$; $R^7$ represents $-CO-$ or $-SO_2-$; $R^8$ represents $-CO-$, or single bond; $R^{12}$ represents $-R^{11}-R^5$; $-R^{11}$ represents $-N(R^5)-$, $-NH-$, $-O-$, $-N(R^{26})-$, $-N[C(=O)R^{27}]-$, $-N[C(=O)NH_2]-$ or $-N[C(=O)NHR^{28}]-$; $R^5$ represents hydrogen atom, $-CH_2C_6H_4COOH$, $-CH_2C_6H_4COOR^{31}$, $-CH_2C_6H_4OH$, $-CH_2C_6H_4OR^{32}$, $-CH_2C_6H_4NH_2$, $-CH_2C_6H_4N(R^{33})_2$, $-CH_2C_6H_4$-azole, $-CH_2C_6H_4NHR^{34}$, or $-CH_2C_6H_4C_6H_4R^{14}$; $R^{14}$ represents an azole group, or $-COOH$; $R^{13}$ represents hydrogen atom, an alkyl group having 1–6 carbon atoms, a haloalkyl group having 1–6 carbon atoms, $-NHC(=O)(CH_2)_mC_6H_5$, $-NHC(=O)R^{29}$, $-NHC(=O)CH(C_6H_5)_2$, $-NH_2$, $-NHR^{30}$, or $-(CH_2)_nC_6H_5$; Z represents C, CH, or N; A represents CH or N; $R^{14}$ represents an azole group, or $-COOH$; $R^{21}$, $R^{22}$, $R^{23}$, $R^{24}$, $R^{25}$, $R^{26}R^{27}$, $R^{28}$, $R^{29}$, $R^{30}$, $R^{31}$, $R^{32}$, $R^{33}$ and $R^{34}$ each independently represents an alkyl group having 1–8 carbon atoms, or a haloaklyl group having 1–8 carbon atoms; m represents 0 or an integer of 1–6; n represents 0 or an integer of 1–6; t represents 0 or 1, with a proviso when Z represents N, then $R^5$ represents hydrogen atom, —$CH_2C_6H_4COOH$, —$CH_2C_6H_4COOR^{31}$, —$CH_2C_6H_4OH$, —$CH_2C_6H_4OR^{32}$, —$CH_2C_6H_4NH_2$, —$CH_2C_6H_4N(R^{33})_2$, —$CH_2C_6H_4$-azole, or —$CH_2C_6H_4NHR^{34}$.

Among compounds shown by general formula (I), particular compounds shown by general formula (II) (hereinafter may be referred as compounds II) were found by the inventors of present invention and disclosed in Japanese Patent Application No. 148,382 (1996) and the inventors of the present invention found that these compounds exhibit anti-renal disease action without hypotensive action, as well as those of aforementioned compounds (I) with further improved pharmacokinetics in the blood.

Chemical formula 4

[General formula (II)]

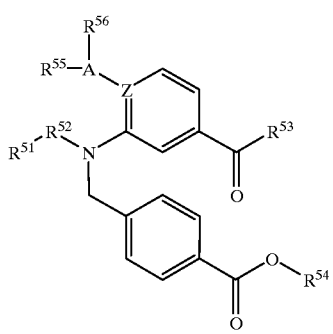

(II)

[wherein, $R^{51}$ represents hydrogen atom, an alkyl group having 1–8 carbon atoms, a haloalkyl group having 1–8 carbon atoms, or —$NR^{57}R^{58}$; $R^{52}$ represents —C(=O)— or single bond; $R^{53}$ represents —$R^{59}$, a 3–7 membered saturated aliphatic cyclic amino group optionally interrupted with nitrogen atom, oxygen atom or sulfur atom, a 3–7 membered saturated aliphatic cyclic amino group containing at least one nitrogen atom substituted with an alkyl group having 1–8 carbon atoms or a haloalkyl group having 1–8 carbon atoms in the ring, a 3–7 membered saturated aliphatic cyclic alkyl group containing at least one nitrogen atom optionally substituted with an alkyl group having 1–8 carbon atoms or a haloalkyl group having 1–8 carbon atoms in the ring, or —$NR^{60}R^{61}$; $R^{54}$ represents hydrogen atom, an alkyl group having 1–8 carbon atoms, a haloalkyl group having 1–8 carbon atoms, —$(CH_2)_m NR^{62}R^{63}$, —$(CH_2)_n R^{64}$, —$(CH^2)_p CH(NR^{65}R^{66})COOR^{67}$, —$R^{68}$—$COOR^{69}$, —$CH(R^{70})OC(=O)OR^{71}$, or —$CH(R^{72})OC(=O)R^{73}$; $R^{60}$ and $R^{61}$ each independently represents hydrogen atom, an alkyl group having 1–8 carbon atoms, a haloalkyl group having 1–8 carbon atoms, or —$(CH_2)_q NR^{74}R^{75}$; $R^{64}$ represents a 3–7 membered saturated aliphatic cyclic amino group optionally interrupted with nitrogen atom, oxygen atom or sulfur atom, a 3–7 membered saturated aliphatic cyclic amino group containing at least one nitrogen atom substituted with an alkyl group having 1–8 carbon atoms or a haloalkyl group having 1–8 carbon atoms in the ring, a 3–7 membered saturated aliphatic cyclic alkyl group containing at least one nitrogen atom optionally substituted with an alkyl group having 1–8 carbon atoms or a haloalkyl group having 1–8 carbon atoms in the ring, or a 3–7 membered unsaturated heterocyclic group; $R^{68}$ represents a 3–7 membered saturated aliphatic cyclic alkylene group containing at least one nitrogen atom optionally substituted with an alkyl group having 1–8 carbon atoms or a haloalkyl group having 1–8 carbon atoms in the ring; $R^{71}$ and $R^{73}$ represent —$(CH_2)_r R^{76}$; $R^{76}$ represents hydrogen atom, an alkyl group having 1–8 carbon atoms, a haloalkyl group having 1–8 carbon atoms, —$NR^{77}R^{78}$, or a 3–8 membered saturated aliphatic cyclic alkyl group; Z represents C, CH, or N; A represents CH or N; $R^{55}$, $R^{56}$, $R^{57}$, $R^{58}$, $R^{59}$, $R^{62}$, $R^{63}$, $R^{65}$, $R^{66}$, $R^{67}$, $R^{69}$, $R^{70}$, $R^{72}$, $R^{74}$, $R^{75}$, $R^{77}$ and $R^{78}$ each independently represents hydrogen atom, an alkyl group having 1–8 carbon atoms, or a haloaklyl group having 1–8 carbon atoms; m, n, p, q and r each independently represents 0 or an integer of 1–6, with a proviso when $R^{54}$ represents hydrogen atom, an alkyl group having 1–8 carbon atoms, or a haloaklyl group having 1–8 carbon atoms, then $R^{53}$ represents a 3–7 membered saturated aliphatic cyclic amino group containing at least one nitrogen atom substituted with an alkyl group having 1–8 carbon atoms or a haloalkyl group having 1–8 carbon atoms in the ring, a 3–7 membered saturated aliphatic cyclic alkyl group containing at least one nitrogen atom optionally substituted with an alkyl group having 1–8 carbon atoms or a haloalkyl group having 1–8 carbon atoms in the ring, or —$NR^{60}R^{61}$ wherein at least one of $R^{60}$ and $R^{61}$ represents —$(CH_2)_q NR^{74}R^{75}$].

The cardiac disease improving agents of the present invention can be indicated to cardiac diseases such as 1) left ventricular asystole (cardiac infarction, dilated cardiomyopathy, hypertensive cardiac diseases), 2) regurgitant valvular diseases (aortic insufficiency, mitral insufficiency), and 3) left and right shunt diseases (patent ductus arteriosus, ventricular septal defect, Valsalva rupture). Further, the agents can also be applied for treatment of diseases contraindicated to ACE inhibitors such as constrictive valvular diseases (aortic stenosis, mitral stenosis), hypertrophic obstructive cardiomyopathy, or cardiac diseases mainly caused by insufficient dilation (hypertrophic cardiomyopathy, constrictive pericarditis, cardiac tamponade). Particularly, these agents can selectively improve cardiac hypertrophy which causes these diseases.

DETAILED DESCRIPTION OF THE INVENTION AND PREFERRED EMBODIMENTS

In the specification of the present invention, an alkyl group includes straight or branched chain alkyl group, for example, methyl group, ethyl group, n-propyl group, isopropyl group, n-butyl group, isobutyl group, sec-butyl group, tert-butyl group, n-pentyl group, isopentyl group, neopentyl group, tert-pentyl group, 1-methylbutyl group, 2-methylbutyl group, 1,2-dimethylpropyl group or 1-ethylpropyl group, n-hexyl group, isohexyl group, 2-ethylbutyl group, n-heptyl group, 5-methylhexyl group, n-octyl group or 4-ethylhexyl group may be illustrated.

An alkyl group having 1–8 carbon atoms may illustrates these alkyl groups and an alkyl group having 1–6 carbon atoms may illustrates those having 1–6 carbon atoms of these alkyl groups.

Also, a haloalkyl group represents aforementioned alkyl groups substituted with 1–17 halogen atoms, and a halogen atom represents, for example, chlorine atom, bromine atom, fluorine atom, or iodine atom, and preferred haloalkyl group may be illustrated with trifluoromethyl group, pentafluoroethyl group, or 4,4,4-trifluorobutyl group.

An azole group means five membered ring having 2–4 hetero atoms (for example nitrogen atom, oxygen atom or sulfur atom), for example, imidazole group, oxazole group, thiazole group, pyrazole group, isoxazole group, isothiazole group, triazole group, oxadiazole group, thiadiazole group, tetrazole group, oxatriazole group or thiatriazole group. A preferred azole group, for example tetrazole group, may be illustrated.

A 3–7 membered saturated aliphatic cyclic amino group optionally interrupted with nitrogen atom, oxygen atom or sulfur atom represents an alkyleneamino group optionally interrupted with a hetero atom (for example, nitrogen atom, oxygen atom or sulfur atom), for example, 1-aziridinyl group, 1-azetidinyl group, 1-pyrrolidinyl group, piperidino group, morpholino group, thiomorpholino group, 1-piperadinyl group, 1-imidazolidinyl group or 1-pyrazolinyl group.

A 3–7 membered saturated aliphatic cyclic amino group having at least one nitrogen atom substituted with an alkyl group having 1–8 carbon atoms or a haloalkyl group having 1–8 carbon atoms in the ring represents, for example, 4-methylpiperazin-1-yl group, 4-ethylpiperazin-1-yl group, 4-propylpiperazin-1-yl group, 4-butylpiperazin-1-yl group, 4-pentylpiperazin-1-yl group, 4-hexylpiperazin-1-yl group, 3-methylimidazolidin-1-yl group, 2-methylpyrazolidin-1-yl group, 4-trifluoromethylpiperazin-1-yl group or 4-trifluoroethylpiperazin-1-yl group may be illustrated.

A 3–7 membered saturated aliphatic cyclic alkyl group having at least one nitrogen atom optionally substituted with an alkyl group having 1–8 carbon atoms or a haloalkyl group having 1–8 carbon atoms in the ring represents, for example, 1-methylaziridinyl group, 1-methylazetidinyl group, 1-methylpyrrolidinyl group, 1-ethylpyrrolidinyl group, 1-propylpyrrolidinyl group, pyrrolidinyl group, 3-methylimidazolidin-4-yl group, 1-methylpyrazolidin-4-yl group, piperidyl group, 1-methylpiperidyl group, 1-ethylpiperidyl group, 1-propylpiperidinyl group, 1-trifluoromethylpyrrohdinyl group, 1-trifluoroethylpyrrolidinyl group, 1-trifluoromethylpiperidyl group or 1-trifluoroethylpiperidyl group.

A 3–7 membered unsaturated heterocyclic group represents a group of 3–7 membered heterocyclic compounds containing 1–7 hetero atoms (for example, nitrogen atom, oxygen atom and sulfur atom), for example, imidazolyl group, oxazolyl group, thiazolyl group, pyrazolyl group, isoxazolyl group, isothiazolyl group, triazolyl group, oxadiazolyl group, thiadiazolyl group, tetrazolyl group, oxatriazolyl group, thiotriazolyl group, thienyl group, furyl group, pyranyl group, pyrrolyl group, pyrazolinyl group, imidazolinyl group, pyridyl group, pyrazinyl group, pyrimidinyl group or pyridazinyl group.

A 3–7 membered saturated aliphatic cyclic alkylene group having at least one nitrogen atom optionally substituted with an alkyl group having 1–8 carbon atoms or a haloalkyl group having 1–8 carbon atoms in the ring may optionally be substituted with the aforementioned alkyl group having 1–8 carbon atoms or haloalkyl group having 1–8 carbon atoms. For example, 1-methylaziridinylene group, 1-methylazetidinylene group, 1-methylpyrrolidinylene group, 1-ethylpyrrolidinylene group, 1-propylpyrrolidinylene group, pyrrolidinylene group, 3-methylimidazolidin-4-ylene group, 1-methylpyrazolidin-4-ylene group, piperidylene group, 1-methylpiperidylene group, 1-ethylpiperidylene group, 1-propylpiperidylene group, 1-trifluoromethylpyrrolidinylene group, 1-trifluoromethyl-piperidylene group or 1-trifluoroethylpiperidylene group may be illustrated.

A 3–8 membered saturated aliphatic cycloalkyl group, for example, cyclopropyl group, cyclobutyl group, cyclopentyl group, cyclohexyl group, cycloheptyl group or cyclooctyl group may be enumerated.

The pharmaceutically acceptable salts of compounds of the present invention include inorganic or organic acid salts, and inorganic or organic base salts thereof. The acid addition salts thereof, for example, hydrochloride, sulfate, methanesulfonate or p-toluenensulfonate, furthermore, dicarboxylic acid salts such as oxalic acid, malonic acid, succinic acid, maleic acid or fumaric acid, and monocarboxylic acid salts such as acetic acid, propionic acid or butyric acid can be illustrated. Furthermore, inorganic bases suitable to form salts thereof, for example, hydroxides, carbonates and hydrogencarbonates of ammonium, sodium, lithium, calcium, magnesium or aluminum are included. Salts of organic bases, for example, mono-, di- and tri-alkylamine salts such as methylamine, dimethylamine and triethylamine, mono-, di-, and trihydroxy-alkylamine salts, guanidine salt, N-methylglucosamine salt and amino acid salts can be enumerated.

Compounds (I) which belong to compounds relating to the present invention can be synthesized from known compounds by similar manners disclosed in detail in Published Japanese Unexamined Patent Application No. 48,651 (1996) except for compounds shown by aforementioned general formula (I) wherein $R^{12}$ represents $R^{35}R^{36}N(CH_2)_m$-oxycarbonylbenzyl group, $R^{37}(CH_2)_n$-oxycarbonylbenzyl group, $R^{40}OOC(NR^{38}\quad R^{39})$—$CH(CH_2)_p$-oxycarbonylbenzyl group ($R^{12}$, $R^{35}$, $R^{36}$, $R^{37}$, $R^{38}$, $R^{39}$, and $R^{40}$ represents same meaning as shown above). Among final aimed compounds, for example, when $R^7$ represents carbonyl group in the aforementioned general formula (I), benzoic acid derivatives shown by general formula (11) are used as starting materials and when $R^7$ represents sulfonyl group, benzenesulfonyl chloride derivatives are used as starting materials instead of benzoic acid derivatives. The starting materials may be suitably selected according to the structure of final aimed compounds in consideration of the type of substituents on benzene ring of the structure of starting materials. For example, when a nitrogen atom is bound at para-position of carbonyl or sulfonyl group of the aimed benzene derivatives, then an amino group or a derivative thereof is selected, when carbon atom is bound, then an alkyl group is selected, when a nitrogen atom is bound at meta-position, then an amino group or a derivative thereof is selected, when oxygen atom is bound, then compounds having hydroxy group may be prepared as starting materials. These starting material benzene derivatives can be prepared per se by known methods.

Hereinafter, a synthetic route for preparation of compounds of general formula (I) in which $R^7$ represents carbonyl group and nitrogen atom binds at meta-position of benzene ring is exemplified.

Chemical Formula 5

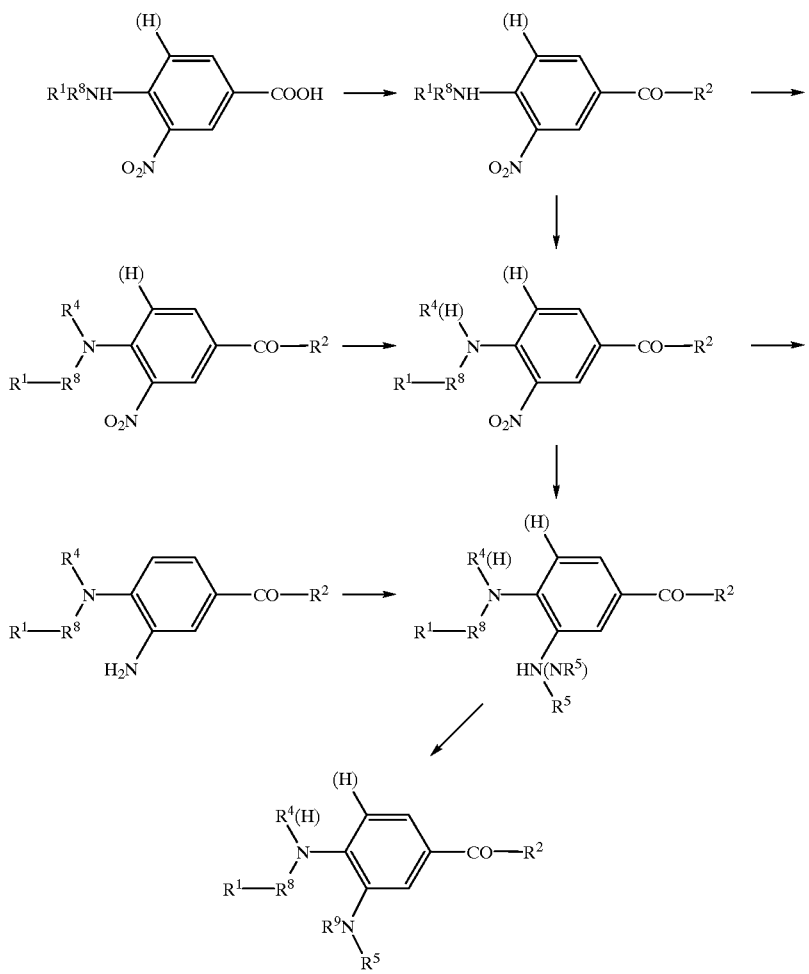

Compounds shown by general formula (I), in which A represents —CH— and $R^7$ represents —SO2—, can be synthesized by a similar methods according to those described in detail in Published Japanese Unexamined Patent Application No. 48,651 (1996).

Furthermore, compounds (II) wherein $R^{35}R^{36}N(CH_2)_m$-oxy-carbonylbenzyl group, $R^{37}(CH_2)_n$-oxycarbonylbenzyl group, or $R^{40}OOC(NR^{38}R^{39})CH(CH_2)_p$-oxycarbonylbenzyl group (wherein $R^{12}$, $R^{35}$, $R^{36}$, $R^{37}$, $R^{38}$, $R^{39}$, and $R^{40}$ represents same meaning as shown above) bound to nitrogen atom of $R^{12}$ in said general formula (I) can be synthesized by similar manners disclosed in detail in specification of Japanese Patent Application No. 148,832 (1996) as shown by the following synthetic route.

Chemical formula 6
[General formula (II)]

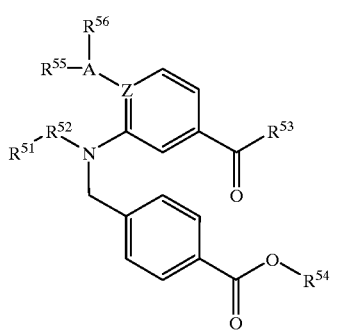

(II)

Chemical Formula 7

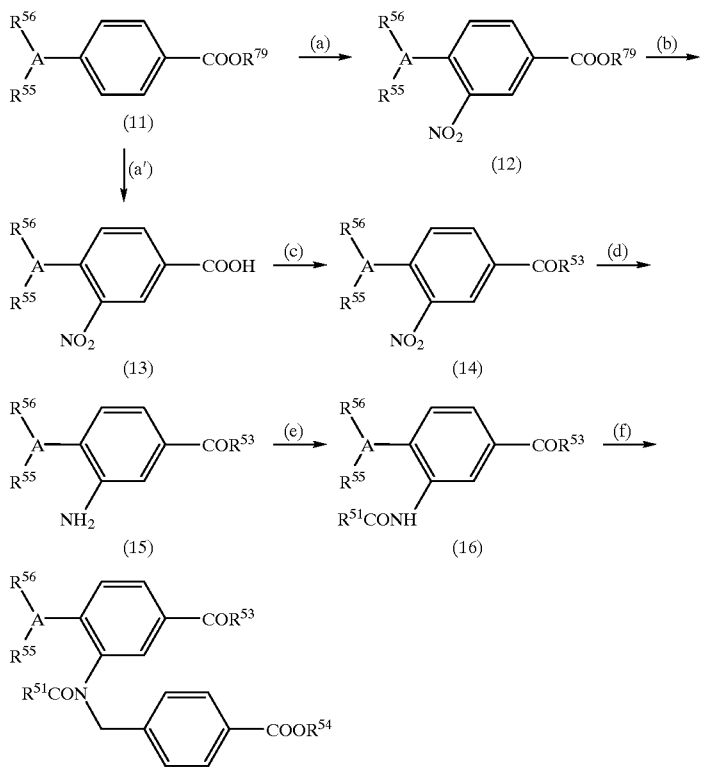

(a), (a') steps

Compounds shown by general formula (11) (wherein, $R^{55}$, $R^{56}$ and A represent same aforementioned meanings, $R^{79}$ represents hydrogen atom or an alkyl group having 1–8 carbon atoms) are dissolved in a solvent such as acetic anhydride, with added fuming nitric acid and caused to react at −10 to 30° C. for 1–10 hours to give compounds shown by general formula (12) (wherein, $R^{55}$, $R^{56}$, $R^{79}$ and A represent same aforementioned meanings).

(b) step

Compounds shown by general formula (12) are dissolved in a solvent such as methanol, ethanol, tetrahydrofuran or dioxane and treated with an aqueous alkaline solution at 10° C. to a temperature below the boiling point of the solvent used. The reaction mixture was cooled and acidified to precipitate compounds shown by general formula (13) (wherein, $R^{55}$, $R^{56}$ and A represent same aforementioned meanings).

(c) step

Compounds shown by general formula (13) are dissolved in a solvent such as chloroform, tetrahydrofuran, benzene, pyridine, or N,N-dimethylformamide and caused to react with a compound capable of converting —COOH group into $COR^{53}$ group ($R^{53}$ represents the same aforementioned meanings) and a suitable condensing agent to give compounds shown by general formula (14) (wherein, $R^{55}$, $R^{56}$, $R^{53}$ and A represent same aforementioned meanings). As an example of the compounds capable of converting —COOH into —$COR^{53}$ morpholine can be illustrated when $R^{53}$ represents morpholino group. For the other $R^{53}$ group, person skilled in the art may suitably select the compounds according to the aimed compounds.

(d) step

Compounds shown by general formula (14) are dissolved in a solvent such as tetrahydrofuran, alcohol or ethyl acetate and a suitable reducing agent such as hydrazine hydrate, and 10% Pd/C, stannic (II) chloride dihydrate, or sodium hydrosulfite is added. The reaction mixture is treated at 0–100° C. to give compounds shown by general formula (15) (wherein, $R^{55}$, $R^{56}$, $R^{53}$ and A represent same aforementioned meanings).

(e) step

Compounds shown by general formula (15) are dissolved in a solvent such as pyridine or N,N-dimethylformamide and caused to react with a compound having desired substituent at −10 to 100° C. to give compounds shown by general formula (16) (wherein, $R^{55}$, $R^{56}$, $R^{53}$, $R^{51}$ and A represent same aforementioned meanings).

(f) step

Compounds shown by general formula (16) are dissolved in a solvent such as dimethylsulfoxide, N,N-dimethylformamide, tetrahydrofuran, tert-butyl methyl ether and caused to react with compounds shown by general formula (18)

$$Y-CH_2(C_6H_4)COOR^{54} \qquad (18)$$

[$R^{54}$ represents the same aforementioned meaning, ($C_6H_4$) represents p-phenylene group, Y represents a releasing group such as a halogen atom] in the presence of sodium hydride or sodium hydroxide at −20 to 100° C. to give compounds shown by general formula (17) (wherein, $R^{55}$, $R^{56}$, $R^{53}$, $R^{51}$, $R^{54}$ and A represent same aforementioned meanings). Protecting groups which may present in these compounds can be removed if required by treatment with an acid and/or a base. The treatment may provides compounds having hydrogen atom for $R^{54}$ group and the following conventional esterification provides compounds having $R^{54}$ with the same aforementioned meanings other than hydrogen atom.

The aromatic compounds or pharmaceutically acceptable salts thereof of the present invention shown by the aforementioned general formula (I) selectively improve aforementioned cardiac diseases such as left ventricular asystole, regurgitant valvular diseases, left and right shunt diseases, and diseases contraindicated to conventional ACE inhibitors such as constrictive valvular diseases without lowering blood pressure, particularly and selectively improve cardiac hypertrophy which causes these diseases. Thus, appropriate treatment of cardiac disease can be carried out with these compounds in combination with a suitable hypotensive, according to the required conditions, for the blood pressure control to maintain desirable blood pressure level.

The present invention is practically explained by the following synthetic examples.

SYNTHETIC EXAMPLE 1

Synthesis of 4-dimethylamino-3-N-[[[4-(2'-dimethylaminoethoxycarbonyl)phenyl]-methyl]valeramido]benzoic acid morpholide (Compound No. 1)

In six mililiters of chloroform, 300 mg of 3-N-[[(4-carboxyphenyl)methyl]valeramido]-4-dimethylaminobenzoic acid morpholide, compound No. 184 disclosed in Published Japanese Unexamined Patent Application No. 48,651 (1996), was dissolved and a catalytic amount of N,N-dimethylformamide and 381 mg of thionyl chloride were added, and the resultant reaction mixture was stirred at room temperature for 2.5 hours. After the reaction, the solvent and excess amount of thionyl chloride were distilled off and 4.5 ml of chloroform was again added. To the resultant reaction mixture, 171 mg of 2-dimethylaminoethanol was added and the mixture was stirred at room temperature for 13 hours. The reaction mixture was mixed with water, neutralized with sodium hydrogencarbonate, and extracted with chloroform. The extract was dried over anhydrous sodium sulfate and the solvent was distilled off The residue was purified with a silica gel column chromatography (Kieselgel 60, 15 g, chloroform/methanol=20/1) to give 288 mg of the titled compound as a white solid mass.

m.p.: 125.5–126.5° C.; $^1$H-NMR (500 MHz, CDCl$_3$) δ: 0.85 (t, 3H), 1.24 (sext, 2H), 1.64 (quint, 2H), 2.11(dt, 1H), 2.26 (dt, 1H), 2.32 (s, 6H), 2.68 (t, 2H), 2.87 (s, 6H), 3.0–3.9 (br, 8H), 4.18(d, 1H), 4.40 (t, 2H), 5.73 (d, 1H), 6.54 (d, 1H), 7.01 (d, 1H), 7.20 (d, 2H) 7.33 (dd, 1H), 7.87 (d, 2H).

SYNTHETIC EXAMPLE 2

Synthesis of 3-N-[[[4-(3'-aminopropoxycarbonyl)phenyl]methyl]valeramido]-4-dimethylaminobenzoic acid morpholide (Compound No. 2)

In 10 ml of chloroform, 500 mg of 3-N-[[(4-carboxyphenyl)methyl]valeramido]-4-dimethylanminobenzoic acid morpholide, compound No. 184 disclosed in Published Japanese Unexamined Patent Application No. 48,651 (1996), was dissolved and a catalytic amount of N,N-dimethylformamide and 640 mg of thionyl chloride were added, and the resultant reaction mixture was stirred at room temperature for two hours. After the reaction, the solvent and excess amount of thionyl chloride were distilled off and 7.5 ml of pyridine was added. To the resultant reaction mixture, 375 mg of 3-tert-butoxycarbonylamino-1-propanol was added and the mixture was stirred at room temperature for 24 hours. The reaction mixture was mixed with water and extracted with ethyl acetate. The extract was washed with water, dried over anhydrous sodium sulfate and the solvent was distilled off. The residue was purified with a silica gel column chromatography (Kieselgel 60, 27 g, hexane/ethyl acetate=1/1) to give 452 mg of an intermediate 3-N-[[[4-(3'-tert-butoxycarbonylaminopropoxycarbonyl)phenyl]methyl]-valeramido]-4-dimethyl-aminobenzoic acid morpholide as a white solid mass.

m.p.: 83.0–85.0° C.

In a mixture of 3.4 ml each of tetrahydrofuran (THF) and ethanol, 452 mg of the intermediate obtained by the above mentioned method was dissolved and 2.3 ml of conc. HCl was gradually added under ice cooling. The reaction mixture was returned to room temperature, stirred for three hours and then the solvent was distilled off. To the residue, 10 ml of water was added. The mixture was neutralized with sodium hydrogencarbonate, and extracted with chloroform. The extract was dried over anhydrous sodium sulfate and the solvent was distilled off. The residue was purified with a silica gel column chromatography to give white crystals of the titled compound.

$^1$H-NMR (500 MHz, CDCl$_3$) δ: 0.85 (t, 3H), 1.25 (sext, 2H), 1.44 (s, 9H), 1.62 (quint, 2H), 1.92 (m, 4H), 2.11 (dt, 1H), 2.28 (dt, 1H), 2.87 (s, 6H), 3.0–3.9 (br, 10H), 4.17 (d, 1H), 5.74 (d, 1H), 6.53 (d, 1H), 7.01 (d, 1H), 7.23 (d, 2H), 7.33 (dd, 1H), 7.86 (d, 2H).

SYNTHETIC EXAMPLE 3

Synthesis of 3-N-[[[[4-(2'-amino-2'-ethoxycarbonyl)ethoxycarbonyl]phenyl]methyl]-valeramido]-4-dimethylaminobenzoic acid morpholide (Compound No. 3)

To 62 ml of chloroform solution containing 3.10 g of 3-N-[[(4-carboxyphenyl)methyl]-valeramido]-4-dimethylaminobenzoic acid morpholide, compound No. 184 disclosed in Published Japanese Unexamined Patent Application No. 48,651 (1996), a catalytic amount of N,N-dimethylformamide and 2.4 ml of thionyl chloride were added, and the resultant reaction mixture was stirred at room temperature for three hours. The reaction mixture was concentrated and the residue was dissolved in a mixture of 31 ml of chloroform and 1.9 ml of triethylamine, and 1.70 g of tert-butoxycarbonyl-L-serine ethyl ester in 31 ml of chloroform was added. The reaction mixture was stirred for two hours at room temperature. Then, the reaction mixture was poured in water and chloroform layer was separated. The chloroform layer was washed with saturated sodium chloride solution. The chloroform solution was dried over anhydrous sodium sulfate, filtered and evaporated to give 4.96 g of yellowish brown foamy substance. The product was purified with a silica gel column chromatography (Kieselgel 60, n-hexane/ethyl acetate=2/3) to give an intermediate 3-N-[[[[4-(2'-tert-butoxycarbonylamino-2'-ethoxycarbonyl)ethoxycarbonyl]phenyl]methyl]valeramido]-4-dimethylaminobenzoic acid morpholide as an yellow oily product.

In a mixture of 19 ml each of THF and ethanol, 2.53 g of the resultant intermediate was dissolved and 13 ml of conc. HCl was added. The reaction mixture was allowed to stand at room temperature for 3.5 hours. The reaction mixture was evaporated and dissolved in chloroform. The chloroform solution was washed with saturated aqueous sodium hydrogencarbonate solution and saturated aqueous sodium chloride solution, dried over anhydrous sodium sulfate, filtered and evaporated to give 2.29 g of pale yellowish brown foamy substance. The product was purified with a silica gel column chromatography (Kieselgel 60, chloroform/methanol=40/1) to give 2.15 g of white foamy titled compound.

$^1$H-NMR (500 MHz, CDCl$_3$) δ: 0.85 (t, 3H, J=7.3 Hz), 1.18–1.39 (m, 2H), 1.26 (t, 3H, J=7.3 Hz), 1.55–1.75 (m, 4H), 2.07–2.14 (m, 1H), 2.25–2.31 (m, 1H), 2.37 (s, 6H), 3.0–3.8 (b, 8H), 3.82 (t, 1H, J=4.8 Hz), 4.17–4.24 (m, 1H), 4.22 (q, 2H, J=7.3 Hz), 4.5–4.56 (m, 2H), 5.71 (dd, 1H, J=2.3, 14.2 Hz), 6.56 (t, 1H, J=2.3 Hz), 7.01 (d, 1H, J=8.2 Hz), 7.21 (d, 2H, J=7.8 Hz), 7.33 (dd, 1H, J=2.3, 8.2 Hz), 7.85 (d, 1H, J=7.8 Hz).

SYNTHETIC EXAMPLE 4

Synthesis of 4-dimethylamino-3-N-[[[[4-(2'-ethoxycarbonylpyrrolidin-4'-yloxy)carbonyl]phenyl]methyl]valeramido]benzoic acid morpholide (Compound No. 4)

To a mixture of 11 ml each of pyridine and N,N-dimethylformamide, 2.22 g of 3-N-[[(4-carboxyphenyl)methyl]valeramido]-4-dimethylaminobenzoic acid morpholide, compound No. 184 disclosed in Published Japanese Unexamined Patent Application No. 48,651 (1996), 1.96 g of dicyclohexylcarbodiimide, 0.29 g of dimethylaminopyridine and 1.36 g of tert-butoxycarbonyl-L-hydroxyproline ethyl ester were added and the mixture was stirred at room temperature for 10 days. The reaction mixture was concentrated and the residue was dissolved in chloroform. The chloroform solution was washed with distilled water and saturated aqueous sodium chloride solution, and dried over anhydrous sodium sulfate. The dried extract was filtered and concentrated to give 5.68 g of pale yellow oily mass. The oily mass was purified with a silica gel column chromatography (LiChroprep Si 60, n-hexane/ethyl acetate=1/2) to give 1.33 g of a colorless oily intermediate 4-dimethylamino-3-N-[[[[4-(1'-tert-butoxycarbonyl-2'-ethoxycarbonylpyrrolidin-4'-yloxy)carbonyl]phenyl]methyl]-valeramido]benzoic acid morpholide.

In a mixture of 10 ml each of THF and ethanol 1.33 g of the resultant intermediate was dissolved and seven milliliters of conc. HCl was added. The reaction mixture was allowed to stand at room temperature for 3.5 hours. The reaction mixture was evaporated and dissolved in chloroform. The chloroform solution was washed with saturated aqueous sodium hydrogencarbonate solution and saturated aqueous sodium chloride solution, dried over anhydrous sodium sulfate, filtered and evaporated to give 1.16 g of colorless oily product. The product was purified with a silica gel column chromatography (Kieselgel 60, chloroform/methanol=40/1) to give 0.95 g of colorless oily titled compound.

$^1$H-NMR (500 MHz, CDCl$_3$) δ: 0.85 (t, 3H, J=7.3 Hz), 1.2–1.3 (m, 2H), 1.29 (t, 3H, J=7.3 Hz), 1.5–1.85 (m, 3H), 2.07–2.14 (m, 1H), 2.22–2.3 (m, 2H), 2.34–2.39 (m, 1H), 2.88 (s, 6H), 3.0–3.85 (b, 8H), 3.15 (d, 1H, J=17.9 Hz), 3.43 (dd, 1H, J=5.0, 12.4 Hz), 4.01 (t, 1H, J=7.8 Hz), 4.15–4.2 (m, 1H), 4.21 (q, 2H, J=7.3 Hz), 5.97 (b, 1H), 5.74 (d, 1H, J=14.2 Hz), 6.53 (t, 1H, J=1.8 Hz), 7.01 (d, 1H, J=8.3 Hz), 7.21 (d, 2H, J=8.3 Hz), 7.33 (dd, 1H, J=2.3, 8.3 Hz), 7.86 (d, 2H, J=8.3 Hz).

Hereinafter, physical properties of compounds prepared by the above mentioned methods and those disclosed in Published Japanese Unexamined Patent Application No. 48,651 (1996) are enumerated.

4-(N-n-Amyl-N-methyl)amino-3-[(4-carboxyphenyl)methyl]aminobenzoic acid morpholide (Compound No. 5)

$^1$H-NMR (500 MHz, CDCl$_3$) δ: 0.86 (t, 3H), 1.22–1.35 (m, 4H), 1.48 (quint, 2H), 2.61 (s, 3H), 2.85 (t, 2H), 3.20–3.85 (br, 8H), 4.46 (s, 2H), 5.39 (br, 1H), 6.49 (d, 1H), 6.73 (dd, 1H), 7.03 (d, 1H), 7.43 (d, 2H), 8.05 (d, 2H).

3-[(4-Carboxyphenyl)methyl]amino-4-hexylbenzoic acid morpholide (Compound No. 6)

m.p.: 205–209.5° C.; $^1$H-NMR (500 MHz, CDCl$_3$) δ: 0.82 (t, 3H), 1.2–1.3 (m, 4H), 1.32 (bquint, 2H), 1.58 (quint, 2H), 2.45 (t, 2H), 3.0–4.9 (br, 8H), 4.26 (s, 2H), 6.43 (d, 1H), 6.65 (dd, 2H), 7.01 (d, 1H), 7.36 (d, 2H), 7.98 (d, 2H).

3-N-[[(4-Carboxyphenyl)methyl)valeramido]-4-dimethylaminobenzoic acid morpholide (Compound No. 7)

$^1$H-NMR (500 MHz, CDCl$_3$) δ: 0.85 (t, 3H), 1.2–1.3 (m, 2H), 1.5–1.6 (m, 2H), 2.10 (dt, 1H), 2.35 (dt, 1H), 2.87 (s, 6H), 3.2–3.7 (br, 8H), 4.22 (d, 1H), 5.48 (d, 1H), 6.89 (d, 1H), 7.02 (d, 2H), 7.1–7.2 (m, 5H), 7.31 (dd, 1H), 7.53 (d, 1H), 7.7–7.8 (m, 2H).

4-Methyl-3-N-[[4-(carboxyphenyl)methyl]valeramido]benzoic acid morpholide (Compound No. 8)

$^1$H-NMR (500 MHz, CDCl$_3$) δ: 0.82 (t, 3H), 1.20–1.25 (m, 2H), 1.58 (quint), 1.89 (dt, 1H), 2.00 (dt, 1H), 2.18 (s, 3H), 2.80–3.25 (b, 2H), 3.35–3.85 (b, 6H), 4.18 (d, 1H), 5.55 (d, 1H), 6.71 (s, 1H), 7.34 (d, 2H), 7.36 (s, 2H), 7.97 (d, 2H).

4-Dimethylamino-3-N-[2'-[(1H-tetrazol-5-yl)biphenyl-4-yl]methyl]valeramido]benzoic acid morpholide (Compound No. 11)

m.p.: 102.0–105.0° C.; $^1$H-NMR (500 MHz, d$_6$-DMSO) δ: 0.82 (t, 3H), 1.2–1.3 (m, 2H), 1.5–1.6 (m, 2H), 2.10 (dt, 1H), 2.35 (dt, 1H), 2.87 (s, 6H), 3.2–3.7 (br, 8H), 4.22 (d, 1H), 5.48 (d, 1H), 6.89 (d, 1H), 7.02 (d, 2H), 7.1–7.2 (m, 5H), 7.31 (dd, 1H), 7.53 (d, 1H), 7.7–7.8 (m, 2H).

4-Dimethylamino-3-N-[[4-(1H-tetrazol-5-yl)phenylmethyl]valeramido]benzoic acid morpholide (Compound No. 13)

$^1$H-NMR (500 MHz, CDCl$_3$) δ: 0.79 (t, 3H), 1.22 (tq, 2H), 1.63 (quint, 2H), 2.23 (dt, 1H), 2.31 (dt, 1H), 2.92 (s, 6H), 3.0–3.85 (b, 8H), 4.21 (d, 1H), 5.72 (d, 1H), 6.69 (s, 1H), 7.05 (d, 1H), 7.29 (d, 2H), 7.37 (d, 1H), 8.00 (d, 2H).

4-Dimethylamino-3-N-[[[4-(3'-dimethylaminopropoxycarbonyl)phenyl]methyl]valeramido]benzoic acid morpholide (Compound No 15)

m.p.: 128.0–129.0° C.; $^1$H-NMR (500 MHz, CDCl$_3$) δ: 0.85 (t, 3H), 1.24 (sext, 2H), 1.62 (quint, 2H), 1.92 (quint, 2H), 2.11 (dt, 1H), 2.2–2.4 (m, 7H), 2.41 (t, 2H), 2.87 (s, 6H), 3.0–3.9 (br, 8H), 4.17 (d, 1H), 4.34 (t, 2H), 5.73 (d, 1H), 6.54 (d, 1H), 7.01 (d, 1H), 7.22 (d, 2H), 7.33 (dd, 1H), 7.86 (d, 2H).

3-N-[[[4-(2'-Dimethylaminoethoxycarbonyl)phenyl]methyl]valeramido]-4-isopropyl-benzoic acid morpholide (Compound No. 16)

m.p.: 106.5–110° C.; $^1$H-NMR (500 MHz, CDCl$_3$) δ: 0.83 (t, 3H, J=7.3 Hz), 1.18 (d, 3H, J=6.9 Hz), 1.21 (d, 3H, J=6.9 Hz), 1.18–1.25 (m, 2H), 1.54–1.8 (m, 3H), 1.88–1.94 (m, 1H), 1.98–2.04 (m, 1H), 2.33 (s, 6H), 2.70 (t, 2H, J=6.0 Hz), 2.75–3.95 (b, 8H), 3.01–3.07 (m, 1H), 3.99 (d, 1H, J=14.2 Hz), 4.42 (t, 2H, J=6.0 Hz), 5.72 (d, 1H, J=14.2 Hz), 6.59 (d, 1H, J=1.6 Hz), 7.27 (d, 2H, J=8.3 Hz), 7.43 (dd, 1H, J=1.6, 8.0 Hz), 7.46 (d, 1H, J=8.0 Hz), 7.94 (d, 2H, J=8.3 Hz).

3-N-[[[4-(3'-Dimethylamino-1'-propoxycarbonyl)phenyl]methyl]valeramido]-4-isopropylbenzoic acid morpholide (Compound No. 17)

m.p.: 95–98.5° C.; $^1$H-NMR (500 MHz, CDCl$_3$) δ: 0.83 (t, 3H, J=7.3 Hz), 1.18 (d, 3H, J=6.9 Hz), 1.21 (d, 3H, J=6.9 Hz), 1.54–1.7 (m, 4H), 1.88–2.04 (m, 4H), 2.25 (s, 6H), 2.42 (t, 2H, J=6.9 Hz), 2.85–3.9 (b, 8H), 3.04 (quint, 1H, J=6.9 Hz), 3.99 (d, 1H, J=14.2 Hz), 4.37 (t, 2H, J=6.9 Hz), 5.72 (d, 1H, J=14.2 Hz), 6.59 (d, 1H, J=1.4 Hz), 7.27 (d, 2H, J=7.8 Hz), 7.43 (dd, 1H, J=1.4, 7.8 Hz), 7.46 (d, 1H, J=7.8 Hz), 7.92 (d, 2H, J=7.8 Hz).

3-N-[[[4-(2'-Diethylaminoethoxycarbonyl)phenyl]methyl]valeramido]-4-isopropylbenzoic acid morpholide (Compound No. 18)

m.p.: 78.0–82.0° C.

$^1$H-NMR (500 MHz, CDCl$_3$) δ: 0.83 (t, 3H), 1.06 (t, 6H), 1.1–1.3 (m, 8H), 1.58 (quint, 2H), 1.92 (dt, 1H), 2.01 (dt, 1H), 2.62 (q, 4H), 2.84 (t, 2H), 3.04 (sext, 1H), 3.2–3.9 (br, 8H), 4.01 (d, 1H), 4.38 (t, 2H), 5.69 (d, 1H), 6.60 (s, 1H), 7.27 (d, 2H), 7.4–7.5 (m, 2H), 7.92 (d, 2H).

3-N-[[[4-(2'-Morpholinoethoxycarbonyl)pheny]methyl]valeramido]-4-isoropylbenzoic acid morpholide (Compound No. 19)

m.p.: 94.5–98.0° C.; $^1$H-NMR (500 MHz, CDCl$_3$) δ: 0.83 (t, 3H), 1.1–1.3 (m, 2H), 1.59 (quint, 2H), 1.92 (dt, 1H), 2.01 (dt, 1H), 2.56 (t, 4H), 2.76 (t, 2H), 3.04 (sext, 1H), 2.9–3.9 (br, 8H), 3.71 (t, 4H), 3.99 (d, 1H), 4.45 (t, 2H), 5.72 (d, 1H), 6.60 (d, 1H), 7.28 (d, 2H), 7.4–7.5 (m, 2H), 7.92 (d, 2H).

3-[[4-(Carboxyphenyl)methyl]valeramido]-4-dimethylaminobenzoic acid 4'-methyl-piperazide (Compound No. 20)

m.p.: 115.0–116.0° C.; $^1$H-NMR (500 MHz, CDCl$_3$) δ: 0.86 (t, 3H), 1.24 (tq, 2ll), 1.64 (ddt, 5H), 2.08 (dt, 1H), 2.30 (dt, 1H), 2.38 (s, 3H), 2.40–3.70 (br, 8H), 2.92 (s, 6H), 4.08 (d, 1H), 5.88 (d, 1H), 6.35 (s, 1H), 7.02 (d, 1H), 7.14 (bs, 2H), 7.35 (d, 1H), 7.87 (d, 2H).

Compounds having structural formulae shown in Table 1 can be enumerated as preferred compounds.

Chemical formula 8

[General formula (I)]

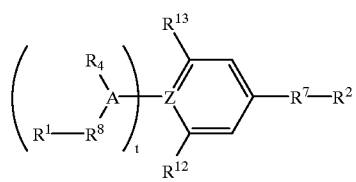

(I)

The cardiac diseases improving agents of the present invention contain compounds I and II shown by aforementioned general formula (I) or pharmacologically acceptable salts thereof as effective ingredients, and are administered orally or parenterally, singly or in combination with pharmacologically acceptable pharmaceutical carriers.

Oral formulations can be illustrated, for example, capsules, tablets, powder preparations, granules, solid preparations, syrups and suspensions.

Parenteral formulations can be illustrated, for example, injection preparations, sublingual preparations, ointments and suppositories.

However, oral and long term administration is preferable in consideration of chronic symptoms of cardiac diseases.

Oral preparations can be prepared from aforementioned compounds per se, however, powder preparations, tablets, granules or capsules may be prepared with a suitable preparation procedure by admixing with compounds of conventional pharmaceutical carriers, for example, starch, lactose, saccharose, mannit, carboxymethylcellulose, corn starch, microcrystalline celluloses, and inorganic salts.

In addition, other pharmacologically acceptable agents such as binders, disintegrators, surfactants, and lubricants may be added.

Furthermore, parenteral preparations such as injection preparations may be illustrated. These preparations may be prepared in suitable forms such as intramuscular or intravenous injection preparations together with a diluents such as distilled water for injection, saline, aqueous glucose solution, vegetable oil for injection, propylene glycol, and polyethylene glycol. In some cases, bactericides, preservatives and stabilizers may be added.

The compounds of the present invention exhibit efficacy for prevention and treatment of cardiac diseases such as cardiac infarction and hypertrophy without lowering blood pressure by oral or parenteral administration at doses of 1–200 mg/kg in one to several portions daily.

The present invention will be practically explained by the following examples.

EXAMPLE 1

Acute Toxicity

Female 5-week-old ICR mice were divided to groups each having five animals and acclimated for a week. Compound Nos. 1–3, 7, 8, 11 and 13 each was dissolved or dispersed in 0.5% methylcelulose aqueous solution, respectively, and orally administered once at a dose of 500 mg/kg, then the number of dead animals was counted after six days. No dead animals was found in any compound.

EXAMPLE 2

Affinity to angiotensin II receptor

The affinity to type 1 and 2 receptors of angiotensin 11 was estimated with a binding assay method in a similar manner described in Biochem. Pharmacol., 33: 4057–4062 (1984). Practically, determination of total binding of each compound was carried out as follows. A mixture of 0.025 ml

TABLE 1

| No | $R^1$ | A | Z | $R^2$ | $R^4$ | $R^7$ | $R^8$ | $R^{12}$ | $R^{13}$ |
|----|-----|---|---|-----|-----|-----|-----|--------|--------|
| 1 | Me | N | C | NC$_4$H$_8$O | Me | CO | SB | N(CO-nBu)CH$_2$Ph-4-COOCH$_2$CH$_2$N(Me)$_2$ | H |
| 2 | Me | N | C | NC$_4$H$_8$O | Me | CO | SB | N(CO-nBu)CH$_2$Ph-4-COOCH$_2$CH$_2$CH$_2$NH$_2$ | H |
| 3 | Me | N | C | NC$_4$H$_8$O | Me | CO | SB | N(CO-nBu)CH$_2$Ph-4-COOCH$_2$CH(COOEt)NH$_2$ | H |
| 4 | Me | N | C | NC$_4$H$_8$O | Me | CO | SB | N(CO-nBu)CH$_2$Ph-4-COO—[pyrrolidine]—COOEt | H |
| 5 | nPen | N | C | NC$_4$H$_8$O | Me | CO | SB | NHCH$_2$Ph-4-COOH | H |
| 6 | nPen | CH | C | NC$_4$H$_8$O | H | CO | SB | NHCH$_2$Ph-4-COOH | H |
| 7 | Me | N | C | NC$_4$H$_8$O | Me | CO | SB | N(CO-nBu)CH$_2$Ph-4-COOH | H |
| 8 | H | CH | C | NC$_4$H$_8$O | H | CO | SB | N(CO-nBu)CH$_2$Ph-4-COOH | H |
| 9 | Me | N | C | NC$_4$H$_8$O | Me | CO | SB | N(CO-nBu)CH$_2$Ph-4-COOH | CF$_3$ |
| 10 | Me | N | C | NC$_4$H$_8$O | Me | CO | SB | N(CO-nBu)CH$_2$Ph-4-COOH | CH$_3$ |
| 11 | Me | N | C | NC$_4$H$_8$O | Me | CO | SB | N(CO-nBu)CH$_2$PhPh-2-CN$_4$H | H |
| 12 | H | CH | C | NC$_4$H$_8$O | H | CO | SB | N(CO-nBu)CH$_2$Ph-4-COOMe | H |
| 13 | Me | N | C | NC$_4$H$_8$O | Me | CO | SB | N(CO-nBu)CH$_2$Ph-4-CN$_4$H | H |
| 14 | Et | N | C | NC$_4$H$_8$O | Et | CO | SB | N(CO-nBu)CH$_2$Ph-4-COOH | H |

(In the Table, SB represents a single bond, in which $R^1$ directly binds with A)

of a predetermined concentration of test compound prepared by dissolving in DMSO, dilution with a buffer attached to the drug discovery system to 2-fold solution, 0.025 ml of a tracer and 0.2 ml of a receptor to make total volume of 0.25 ml was incubated at room temperature for three hours for type 1 angiotensin II ($AT_1$ receptor or at 37° C. for one hour for type 2 ($AT_2$) receptor. The reaction mixture was filtered under suction with CF/C filter paper for $AT_1$ and CF/B filter paper for $AT_2$. The used filter paper having the combination of the tracer and the receptor was determined with a γ-well counter (ARC-500, Aloka). Non-specific binding was determined with a similar manner by adding a large excess amount of displacer. The specific binding of test compound at a predetermined concentration was obtained by subtracting non-specific binding from respective total binding. In $AT_1$ and $AT_2$, a predetermined concentrations of test compound and a control compound were used to give the inhibitory rate, $IC_{50}$ value of 50% inhibition, or binding inhibitory % at 100 μM, for binding of a radioactive ligand (tracer) and the receptor. The results are shown in Table 2.

TABLE 2

| Compound No. | $IC_{50}$ $AT_1$ (nM) | Binding inhibition % at 100 μM | |
|---|---|---|---|
| | | $AT_1$ | $AT_2$ |
| 1 | | 10 | 16 |
| 2 | | 0 | 0 |
| 3 | | 11 | 0 |
| 4 | | 11 | 0 |
| 5 | | 26 | 0 |
| 6 | | 15 | 0 |
| 7 | | 0 | 0 |
| 8 | | 4 | 0 |
| 11 | | 35 | 0 |
| 13 | | 15 | 0 |
| DuP753 | 20 | | 0 |

Following reagents were used:

for $AT_1$

| Receptor | Derived from rabbit adrenal gland |
|---|---|
| Tracer | $^3$H-angiotensin II |
| Control compound (Displacer) | DuP753 |
| | DuP753 | for $AT_2$

| Receptor | Derived from bovine cerebellum |
|---|---|
| Tracer | $^{125}$I-Tyr$^4$-angiotensin II |
| Control compound | Angiotensin II (human) |
| (Displacer) | Angiotensin II (human) |

The results shown in Table 2 reveal that the compounds of the present invention have no inhibitory effect to type 1 receptor. The lack of binding ability to the type 1 receptor indicates that the compounds of the present invention have quite different action mechanism with those of known ACE inhibitors and angiotensin II inhibitors.

EXAMPLE 3

Hypotensive Action

The compounds of the present invention and a comparative compound, Dup 753, were orally administered by gavage to rats with renal diseases and hypotensive action was determined. Rats with experimental renal disease were prepared with conventional method by ligating branch of renal artery. That is, female Sprague-Dawley rats were anesthetized, left renal hilus was exposed and three of four second branches of renal artery were ligated remaining one branch. One week later, further right renal hilus including artery, vein and ureter was ligated to reduce renal fiction up to about ⅛ to those of normal animals. Rats were divided to make eight animals in one group, and 20 mg/kg of one test compound and water as a control were administered to each group. After two days, systolic blood pressure was determined with a blood pressure determination apparatus using tail cuff method (UR5000, Ueda Manufacturing Co., Ltd.). The values of average blood pressure are shown in Table 3.

TABLE 3

| Compound No. | Blood pressure (mmHg) |
|---|---|
| 1 | 205 |
| 2 | 203 |
| 3 | 204 |
| 4 | 200 |
| 5 | 195 |
| 7 | 195 |
| 8 | 198 |
| 11 | 199 |
| Control | 210 |
| DuP753 | 130 |

Rats administered with comparative compound, Dup 753, showed marked to the control group, while compounds of the present invention showed no substantial effect on the blood pressure.

EXAMPLE 4

Inhibitory Action of Myocardial Disturbance (1) Test 1:

SHR rats were divided into control group and test group each having three animals and both groups were treated with 3/4NPX, an experimental cardiac hypertrophy model prepared by 3/4 partial nephrectomy, after eight weeks. After 12 weeks, compound No. 1, 4-dimethylamino-3-N-[[[4-(2'-dimethylaminoethoxycarbonyl)phenyl]methyl]-valeramido]benzoic acid morpholide, disolved in drinking water was given ad libitum for four weeks at a dose of 20 mg/kg.

Body weight, blood pressure, blood creatinine (Cr), blood urea nitrogen (BUN), creatinine clearance (CCr) and urinary protein (U-Pro) were determined before administration of compound No. 1 (after 12 weeks) and at the end of administration (after 16 weeks). After the oral administration, kidneys and heart were excised and their weight was determined. The results are shown in Tables 4 and 5.

TABLE 4

| 1) Before administration (After 12 weeks) | | | | | |
|---|---|---|---|---|---|
| BW (g) | BP (mmHg) | Cr(mg/dl) | BUN(mg/dl) | CCr(ml/min) | U-Pro. (mg/day) |

| Control group; | | | | | |
|---|---|---|---|---|---|
| 1 | 369 | 231 | 0.7 | 38 | 1.06 | 73.5 |
| 2 | 318 | 222 | 0.8 | 41 | 0.87 | 66.1 |
| 3 | 335 | 237 | 0.9 | 47 | 0.84 | 94.1 |

TABLE 4-continued

| | 1) Before administration (After 12 weeks) | | | | | |
|---|---|---|---|---|---|---|
| | BW (g) | BP (mmHg) | Cr(mg/dl) | BUN(mg/dl) | CCr(ml/min) | U-Pro. (mg/day) |
| Average | 341 | 230 | 0.8 | 42 | 0.92 | 77.9 |
| ± SD | 26.0 | 7.5 | 0.10 | 4.6 | 0.119 | 14.50 |
| Test group; | | | | | | |
| 1 | 385 | 238 | 0.8 | 44 | 1.03 | 60.8 |
| 2 | 318 | 219 | 0.8 | 41 | 0.83 | 45.0 |
| 3 | 344 | 257 | 0.9 | 48 | 0.78 | 75.4 |
| Average | 349 | 238 | 0.8 | 44 | 0.87 | 60.4 |
| ± SD | 33.8 | 19.0 | 0.0.6 | 3.5 | 0.118 | 15.20 |

BW: body weight BP: blood pressure

| | 2) After administration (After 16 weeks) | | | | | | | | | |
|---|---|---|---|---|---|---|---|---|---|---|
| | BW (g) | BP (mmHg) | Cr (mg/dl) | BUN (mg/dl) | CCr (ml/min) | U-Pro. (mg/day) | KW (g) | RW (%) | HW (g) | RW (%) |
| Control group; | | | | | | | | | | |
| 1 | 423 | 224 | 1.0 | 47 | 0.88 | 88.2 | 1.603 | 0.379 | 1.897 | 0.448 |
| 2 | 357 | 238 | 1.0 | 58 | 0.83 | 100.6 | 1.692 | 0.474 | 1.558 | 0.436 |
| 3 | 376 | 261 | 1.2 | 66 | 0.63 | 138.4 | 1.619 | 0.431 | 1.560 | 0.431 |
| Average | 385 | 241 | 1.1 | 57 | 0.78 | 109.3 | 1.638 | 0.428 | 1.672 | 0.438 |
| ± SD | 34.0 | 18.7 | 0.12 | 9.5 | 0.131 | 25.89 | 0.047 | 0.048 | 0.195 | 0.087 |
| Test group; | | | | | | | | | | |
| 1 | 415 | 247 | 1.0 | 55 | 0.88 | 119.8 | 1.515 | 0.365 | 1.546 | 0.373 |
| 2 | 346 | 221 | 0.9 | 50 | 0.74 | 50.5 | 1.269 | 0.366 | 1.326 | 0.383 |
| 3 | 394 | 229 | 1.2 | 70 | 0.66 | 174.6 | 1.568 | 0.398 | 1.606 | 0.408 |
| Average | 385 | 232 | 1.0 | 58 | 0.76 | 114.6 | 1.451 | 0.376 | 1.493 | 0.388 |
| ± SD | 35.4 | 13.3 | 0.15 | 10.4 | 0.111 | 61.74 | 0.160 | 0.019 | 0.147 | 0.018 |

KW: kidney weight RW: relative weight HW: heart weight

In addition, body, kidneys and heart weight were determined in two normal SHR rats and their relative weight ratios were calculated. Body weight (g); kidney weight (g); relative weight ratio (%); heart weight (g); relative weight (%) were 404, 363; 2.959, 2.789; 0.732, 0.771; 1.345, 1.270; 0.333, 0.350, respectively.

Above results show the decrease of heart weight due to cardiac hypertrophy and decreased inhibition of kidney weight increase. Thus, compound No. 1 inhibited cardiac disturbance without inducing hypotension or kidney disturbance.

(2) Test 2:

Similarly, 3/4 NPX (cardiac hypertrophy model caused by 3/4 partial nephrectomy) was carried out at four weeks point in a control group and test group of SHR rats each having two and three animals. At seven weeks, animals were subjected to the experiment and compound No. 1 was dissolved in drinking water and orally administered at a rate of 20 mg/kg ad libitum.

Body weight, blood pressure, blood creatinine (Cr), blood urea nitrogen (BUN), creatinine clearance (CCr) and urinary protein (U-Pro) were determined before oral administration of compound No. 1 (after 7 weeks) and at 9 and 11 weeks after oral administration. After 11 weeks, kidneys and heart were excised and their weight was determined. The results are shown in Tables 6 and 7. Similar test was carried out in normal two rats and the results are shown in Table 8.

| | 1) Before administration (After 7 weeks) | | | | | |
|---|---|---|---|---|---|---|
| | BW (g) | BP (mmHg) | Cr(mg/dl) | BUN(mg/dl) | CCr(ml/min) | U-Pro. (mg/day) |
| Control group; | | | | | | |
| 1 | 170 | 169 | 0.6 | 42 | 0.51 | 11.7 |
| 2 | 170 | 174 | 0.5 | 44 | 0.57 | 21.5 |
| Average | 170 | 172 | 0.6 | 43 | 0.54 | 16.6 |
| ± SD | 0.0 | 3.5 | 0.07 | 1.4 | 0.055 | 6.93 |
| Test group; | | | | | | |
| 1 | 165 | 160 | 0.5 | 38 | 0.54 | 5.6 |
| 2 | 167 | 159 | 0.5 | 36 | 0.59 | 9.9 |
| 3 | 172 | 171 | 0.5 | 42 | 0.61 | 16.0 |

-continued

| 1) Before administration (After 7 weeks) | | | | | | |
|---|---|---|---|---|---|---|
| | BW (g) | BP (mmHg) | Cr(mg/dl) | BUN(mg/dl) | CCr(ml/min) | U-Pro. (mg/day) |
| Average | 168 | 163 | 0.5 | 39 | 0.58 | 9.8 |
| ± SD | 3.6 | 6.7 | 0.00 | 3.1 | 0.034 | 4.20 |

| 2) After administration (After 9 weeks) | | | | | | |
|---|---|---|---|---|---|---|
| | BW (g) | BP (mmHg) | Cr(mg/dl) | BUN(mg/dl) | CCr(ml/min) | U-Pro. (mg/day) |
| Control group; | | | | | | |
| 1 | 269 | 239 | 0.6 | 50 | 0.97 | 51.9 |
| 2 | 241 | 230 | 0.8 | 58 | 0.62 | 76.5 |
| Average | 255 | 235 | 0.7 | 54 | 0.80 | 64.2 |
| ± SD | 19.8 | 6.4 | 0.14 | 5.7 | 0.248 | 17.44 |
| Test group; | | | | | | |
| 1 | 263 | 205 | 0.6 | 41 | 0.83 | 38.7 |
| 2 | 254 | 219 | 0.8 | 45 | 0.51 | 41.5 |
| 3 | 256 | 214 | 0.8 | 47 | 0.58 | 49.8 |
| Average | 258 | 214 | 0.7 | 44 | 0.64 | 43.3 |
| ± SD | 4.7 | 5.0 | 0.12 | 3.1 | 0.168 | 5.77 |

| 2) After administration (After 11 weeks) | | | | | | | | | | |
|---|---|---|---|---|---|---|---|---|---|---|
| | BW (g) | BP (mmHg) | Cr (mg/dl) | BUN (mg/dl) | CCr (ml/min) | U-Pro. (mg/day) | KW (g) | RW (%) | HW (g) | RW (%) |
| Control group; | | | | | | | | | | |
| 1 | 297 | 239 | 0.8 | 53 | 0.81 | 104.7 | 1.295 | 0.436 | 1.258 | 0.424 |
| 2 | 268 | 263 | 1.0 | 63 | 0.51 | 116.6 | 1.308 | 0.488 | 1.083 | 0.404 |
| Average | 283 | 251 | 0.9 | 58 | 0.66 | 110.7 | 1.302 | 0.462 | 1.171 | 0.414 |
| ± SD | 20.5 | 17.0 | 0.14 | 7.1 | 0.210 | 8.41 | 0.009 | 0.037 | 0.124 | 0.014 |
| Test group; | | | | | | | | | | |
| 1 | 299 | 217 | 0.7 | 44 | 0.79 | 46.9 | 1.364 | 0.456 | 1.113 | 0.372 |
| 2 | 271 | 259 | 0.8 | 50 | 0.55 | 40.5 | 1.319 | 0.487 | 1.018 | 0.376 |
| 3 | 287 | 234 | 1.0 | 58 | 0.67 | 108.7 | 1.368 | 0.477 | 1.106 | 0.385 |
| Average | 286 | 237 | 0.8 | 56 | 0.67 | 65.4 | 1.350 | 0.473 | 1.078 | 0.378 |
| ± SD | 14.0 | 21.2 | 0.15 | 7.0 | 0.117 | 37.66 | 0.027 | 0.016 | 0.053 | 0.007 |

The declined heart weight and significant decrease of urinary protein were observed in the test group, indicating the inhibition of myocardial disturbance by administration of compound No. 1.

EXAMPLE 5

A mixture of 10 mg of compound No. 1, 36 mg of lactose, 150 mg of corn starch, 29 mg of microcrystalline cellulose and 5 mg of magnesium stearate was tableted to make tablets each weighing 230 mg. The tablets can be orally administered to patients with cardiac hypertrophy several times for a day at a dose of one tablet.

What is claimed is:
1. A method for treating cardiac disease, comprising the step of administering to a patient in need of treatment an effective amount of a compound having the following general formula (II) or pharmacologically acceptable salts thereof

Chemical formula 2

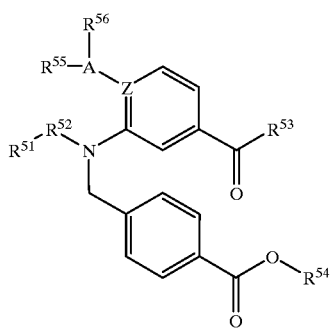

(II)

wherein $R^{51}$ represents hydrogen atom, an alkyl group having 1–8 carbon atoms, a haloalkyl group having 1–8 carbon atoms, or —$NR^{57}R^{58}$; $R^{52}$ represents —C(=O)— or single bond; $R^{53}$ represents —$OR^{59}$, a 3–7 membered saturated aliphatic cyclic amino group optionally interrupted with nitrogen atom, oxygen atom or sulfur atom, a 3–7 membered saturated aliphatic cyclic amino group containing at least one nitrogen atom and substituted with an alkyl group having 1–8 carbon atoms or a haloalkyl group having 1–8 carbon atoms in the ring, or —NR$^{60}$R$^{61}$; R$^{54}$ represents hydrogen atom, an alkyl group having 1–8 carbon atoms, a haloalkyl group having 1–8 carbon atoms, —(CH$_2$)$_m$NR$^{62}$R$^{63}$, —(CH$_2$)$_n$R$^{64}$, —(CH$_2$)$_p$CH(NR$^{65}$R$^{66}$)COOR$^{67}$, —R$^{68}$—COOR$^{69}$, —CH(R$^{70}$)OC(=O)OR$^{71}$, or —CH(R$^{72}$)OC(=O)R$^{73}$; R$^{60}$ and R$^{61}$ each independently represents hydrogen atom, an alkyl group having 1–8 carbon atoms, a haloalkyl group having 1–8 carbon atoms, or —(CH$_2$)$_q$NR$^{74}$R$^{75}$; R$^{64}$ represents a 3–7 membered saturated aliphatic cyclic amino group optionally interrupted with nitrogen atom, oxygen atom or sulfur atom, a 3–7 membered saturated aliphatic cyclic amino group containing at least one nitrogen atom and substituted with an alkyl group having 1–8 carbon atoms or a haloalkyl group having 1–8 carbon atoms in the ring, a 3–7 membered saturated aliphatic cyclic alkyl group containing at least one nitrogen atom and substituted with an alkyl group having 1–8 carbon atoms or a haloalkyl group having 1–8 carbon atoms in the ring, or a 3–7 membered unsaturated heterocyclic group; R$^{68}$ represents a 3–7 membered saturated aliphatic cyclic alkylene group containing at least one nitrogen atom and substituted with a alkyl group having 1–8 carbon atoms or a haloalkyl group having 1–8 carbon atoms in the ring; R$^{71}$ and R$^{73}$ represent —(CH$_2$)$_r$R$^{76}$; R$^{76}$ represents hydrogen atom, an alkyl group having 1–8 carbon atoms, a haloalkyl group having 1–8 carbon atoms, —NR$^{77}$R$^{78}$, or a 3–8 membered saturated aliphatic cyclic alkyl group; Z represents C[, CH, or N]; A represents CH or N; R$^{55}$, R$^{56}$, R$^{57}$, R$^{58}$, R$^{59}$, R$^{62}$, R$^{63}$, R$^{65}$, R$^{66}$, R$^{67}$, R$^{69}$, R$^{70}$, R$^{72}$, R$^{74}$, R$^{75}$, R$^{77}$ and R$^{78}$ each independently represents hydrogen atom, an alkyl group having 1–8 carbon atoms, or a haloalkyl group having 1–8 carbon atoms; m, q and r each independently represents an integer of 1–6; n and p each independently represents 0 or an integer of 1–6, with a proviso when R$^{54}$ represents hydrogen atom, an alkyl group having 1–8 carbon atoms, or a haloalkyl group having 1–8 carbon atoms, then R$^{53}$ represents a 3–7 membered saturated aliphatic cyclic amino group containing at least one nitrogen atom and substituted with an alkyl group having 1–8 carbon atoms or a haloalkyl group having 1–8 carbon atoms in the ring, a 3–7 membered saturated aliphatic cyclic alkyl group containing at least one nitrogen atom and substituted with an alkyl group having 1–8 carbon atoms or a haloalkyl group having 1–8 carbon atoms in the ring, or —NR$^{60}$R$^{61}$ wherein at least one of R$^{60}$ and R$^{61}$ represent —(CH$_2$)$_q$NR$^{74}$R$^{75}$.

2. The method according to claim 1, wherein R$^{51}$ represents an alkyl group having 1–8 carbon atoms, a haloalkyl group having 1–8 carbon atoms; R$^{52}$ represents —C(=O)—; R$^{53}$ represents—OR$^{59}$, a 3–7 membered saturated aliphatic cyclic amino group optionally interrupted with nitrogen atom, oxygen atom or sulfur atom, a 3–7 membered saturated aliphatic cyclic amino group containing at least one nitrogen atom and substituted with an alkyl group having 1–8 carbon atoms or a haloalkyl group having 1–8 carbon atoms in the ring, or —NR$^{60}$R$^{61}$; R$^{54}$ represents —(CH$_2$)$_m$NR$^{62}$R$^{63}$, —(CH$_2$)$_n$R$^{64}$, —(CH$_2$)$_p$CH(NR$^{65}$R$^{66}$)COOR$^{67}$, —R$^{68}$—COOR$^{69}$, —CH(R$^{70}$)OC(=O)OR$^{71}$, or —CH(R$^{72}$)OC(=O)R$^{73}$; R$^{60}$ and R$^{61}$ each independently represents hydrogen atom, an alkyl group having 1–8 carbon atoms, a haloalkyl group having 1–8 carbon atoms, or —(CH$_2$)$_q$NR$^{74}$R$^{75}$; R$^{64}$ represents a 3–7 membered saturated aliphatic cyclic amino group optionally interrupted with nitrogen atom, oxygen atom or sulfur atom, a 3–7 membered saturated aliphatic cyclic amino group containing at least one nitrogen atom and substituted with an alkyl group having 1–8 carbon atoms or a haloalkyl group having 1–8 carbon atoms in the ring, or a 3–7 membered unsaturated heterocyclic group; R$^{68}$ represents a 3–7 membered saturated aliphatic cyclic alkylene group containing at least one nitrogen atom and substituted with an alkyl group having 1–8 carbon atoms or a haloalkyl group having 1–8 carbon atoms in the ring; R$^{71}$ and R$^{73}$ represent —(CH$_2$)$_r$R$^{76}$; R$^{76}$ represents hydrogen atom, an alkyl group having 1–8 carbon atoms, a haloalkyl group having 1–8 carbon atoms, —NR$^{77}$ R$^{78}$, or a 3–8 membered saturated aliphatic cyclic alkyl group; Z represents C; A represents CH or N; R$^{55}$, R$^{56}$, R$^{57}$, R$^{58}$, R$^{59}$, R$^{62}$, R$^{63}$, R$^{65}$, R$^{66}$, R$^{67}$, R$^{69}$, R$^{70}$, R$^{72}$, R$^{74}$, R$^{75}$, R$^{77}$ and R$^{78}$ each independently represents hydrogen atom, an alkyl group having 1–8 carbon atoms, or a haloalkyl group having 1–8 carbon atoms; m, q and r each independently represents an integer of 1–6; n and p each independently represents 0 or an integer of 1–6.

3. The method according to claim 1, wherein R$^{51}$ represents an alkyl group having 1–8 carbon atoms, a haloalkyl group having 1–8 carbon atoms; R$^{52}$ represents —C(=O)—; R$^{53}$ represents —OR$^{59}$, a 3–6 membered saturated aliphatic cyclic amino group optionally interrupted with nitrogen atom, oxygen atom or sulfur atom, a 3–6 membered saturated aliphatic cyclic amino group containing at least one nitrogen atom and substituted with an alkyl group having 1–6 carbon atoms or a haloalkyl group having 1–6 carbon atoms in the ring, or —NR$^{60}$R$^{61}$; R$^{54}$ represents —(CH$_2$)$_m$NR$^{62}$R$^{63}$, —(CH$_2$)$_n$R$^{64}$, —(CH$_2$)$_p$CH(NR$^{65}$R$^{66}$)COOR$^{67}$, —R$^{68}$—COOR$^{69}$, —CH(R$^{70}$)OC(=O)OR$^{71}$, or —CH(R$^{72}$)OC(=O)R$^{73}$; R$^{60}$ and R$^{61}$ each independently represents hydrogen atom, an alkyl group having 1–5 carbon atoms, a haloalkyl group having 1–5 carbon atoms, or —(CH$_2$)$_q$NR$^{74}$R$^{75}$; R$^{64}$ represents a 3–6 membered saturated aliphatic cyclic amino group optionally interrupted with nitrogen atom, oxygen atom or sulfur atom, a 3–6 membered saturated aliphatic cyclic amino group containing at least one nitrogen atom and substituted with an alkyl group having 1–6 carbon atoms or a haloalkyl group having 1–6 carbon atoms in the ring, or a 3–6 membered unsaturated heterocyclic group; R$^{68}$ represents a 3–6 membered saturated aliphatic cyclic alkylene group containing at least one nitrogen atom and substituted with an alkyl group having 1–6 carbon atoms or a haloalkyl group having 1–6 carbon atoms in the ring; R$^{71}$ and R$^{73}$ represent —(CH$_2$)$_r$R$^{76}$; R$^{76}$ represents hydrogen atom, an alkyl group having 1–5 carbon atoms, a haloalkyl group having 1–5 carbon atoms, —NR$^{77}$R$^{78}$, or a 3–6 membered saturated aliphatic cyclic alkyl group; Z represents C; A represents CH, or N; R$^{55}$, R$^{56}$, R$^{57}$, R$^{58}$, R$^{59}$, R$^{62}$, R$^{63}$, R$^{65}$, R$^{66}$, R$^{67}$, R$^{69}$, R$^{70}$, R$^{72}$, R$^{74}$, R$^{75}$, R$^{77}$ and R$^{78}$ each independently represents hydrogen atom, an alkyl group having 1–5 carbon atoms, or a haloalkyl group having 1–5 carbon atoms; m, q and r each independently represents an integer of 1–4; n and p each independently represents 0 or an integer of 1–4.

4. The method according to claim 1, wherein R$^{53}$ represents a 3–6 membered saturated aliphatic cyclic amino group containing at least one nitrogen atom and substituted with an alkyl group having 1–6 carbon atoms or a haloalkyl group having 1–6 carbon atoms in the ring, or —NR$^{60}$R$^{61}$ wherein at least one of R$^{60}$ and R$^{61}$ represents —(CH$_2$)$_q$NR$^{74}$R$^{75}$.

5. The method according to claim 1, wherein R$^{54}$ represents —(CH$_2$)$_m$NR$^{62}$R$^{63}$, —(CH$_2$)$_n$R$^{64}$, —(CH$_2$)$_p$CH(NR$^{65}$R$^{66}$)COOR$^{67}$, —R$^{68}$ —COOR$^{69}$, —CH(R$^{70}$)OC(=O)OR$^{71}$, or —CH(R$^{72}$)OC(=O)R$^{73}$.

6. The method according to claim 1, wherein $R^{53}$ represents a 3–7 membered saturated aliphatic cyclic amino group optionally interrupted with oxygen atom or sulfur atom.

7. The method according to claim 1, wherein $R^{53}$ represents a morpholino group.

* * * * *